(12) United States Patent
Abboud et al.

(10) Patent No.: US 10,413,383 B2
(45) Date of Patent: Sep. 17, 2019

(54) MULTI-DIAMETER DRILL BIT

(71) Applicant: THE RESEARCH FOUNDATION FOR THE STATE UNIVERSITY OF NEW YORK, Albany, NY (US)

(72) Inventors: Marcus Abboud, Setauket, NY (US); Sihana Hana Rugova, Stony Brook, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 15/738,248

(22) PCT Filed: Jun. 23, 2016

(86) PCT No.: PCT/IB2016/001010
§ 371 (c)(1),
(2) Date: Dec. 20, 2017

(87) PCT Pub. No.: WO2016/207728
PCT Pub. Date: Dec. 29, 2016

(65) Prior Publication Data
US 2018/0168772 A1 Jun. 21, 2018

Related U.S. Application Data

(60) Provisional application No. 62/183,448, filed on Jun. 23, 2015.

(51) Int. Cl.
*A61C 3/02* (2006.01)
*A61C 8/00* (2006.01)
*A61B 17/16* (2006.01)

(52) U.S. Cl.
CPC ............. *A61C 3/02* (2013.01); *A61C 8/0089* (2013.01); *A61B 17/1615* (2013.01)

(58) Field of Classification Search
CPC ...... A61C 8/0089; A61C 3/02; A61B 17/1615
See application file for complete search history.

(56) References Cited

U.S. PATENT DOCUMENTS

| 4,602,900 A | 7/1986 | Arpaio, Jr. et al. |
| 5,871,356 A * | 2/1999 | Guedj ................ A61C 8/0022 433/165 |

(Continued)

FOREIGN PATENT DOCUMENTS

| DE | 29904042 U1 | 9/1999 |
| EP | 1293173 A2 | 3/2003 |

(Continued)

OTHER PUBLICATIONS

International Search Report dated Dec. 1, 2016 issued in PCT/IB2016/001010.

(Continued)

*Primary Examiner* — Ralph A Lewis
(74) *Attorney, Agent, or Firm* — Scully, Scott, Murphy & Presser, P.C.

(57) ABSTRACT

A multi-diameter drill bit for implant bed preparation is provided. The drill bit has a drill shank that can be coupled with a driving tool to transfer drilling torques and forces to a drill body distal to the drill shank and a drill tip distal to the drill body. The drill body is divided into a first cylindrical portion having a first diameter and a second cylindrical portion having a second diameter. The drill tip is connected to the first cylindrical portion of the drill body and defines multiple first land areas and multiple cutting lips each at least partially bordering a respective first land areas. The second diameter is greater than the first diameter to define a plurality of faces of second lands at the interface between the (Continued)

first cylindrical portion and the second cylindrical portion, for reducing friction between the drill bit and surrounding bone tissue.

13 Claims, 13 Drawing Sheets

(56) References Cited

U.S. PATENT DOCUMENTS

| | | | |
|---|---|---|---|
| 6,602,029 B1* | 8/2003 | George | B23B 51/02 407/23 |
| 9,022,783 B2* | 5/2015 | Huwais | A61C 8/0089 433/165 |
| 2002/0119418 A1* | 8/2002 | Matsutani | B23P 15/32 433/102 |
| 2005/0170311 A1* | 8/2005 | Tardieu | A61C 1/084 433/76 |
| 2006/0093448 A1 | 5/2006 | Kelsey | |
| 2006/0210949 A1 | 9/2006 | Stoop | |
| 2007/0298376 A1 | 12/2007 | Kmiecz et al. | |
| 2008/0085488 A1 | 4/2008 | Lazarof | |
| 2009/0305189 A1* | 12/2009 | Scortecci | A61C 8/0022 433/165 |
| 2011/0250561 A1* | 10/2011 | Choi | A61C 3/02 433/126 |
| 2011/0275032 A1 | 11/2011 | Tardiue et al. | |
| 2013/0136552 A1* | 5/2013 | Ono | B23B 51/009 408/1 R |
| 2013/0244202 A1* | 9/2013 | Chen | A61C 8/0022 433/165 |
| 2013/0317508 A1* | 11/2013 | Ellis | A61B 17/1615 606/80 |
| 2014/0113245 A1 | 4/2014 | Heo | |
| 2014/0220508 A1 | 8/2014 | Scalise et al. | |

FOREIGN PATENT DOCUMENTS

| | | |
|---|---|---|
| KR | 10-0946344 B1 | 3/2010 |
| WO | WO 2009/066935 A1 * | 5/2009 |

OTHER PUBLICATIONS

Dolan, E.B. et al., "Heat-shock-induced cellular responses to temperature elevations occurring during orthopaedic cutting", J. R. Soc. Interface (2012), vol. 9, pp. 3503-3513.

Extended European Search Report issued in corresponding EP Patent Application No. 16813798.2 dated Jan. 18, 2019.

* cited by examiner

Prüfprotokoll ibb Zerspanungstechnik GmbH - Hans-Katzer-Straße 3 - D-51503 Rösrath
Tel.: +49 (0) 2205 92055-0 - eMail: service@ibb-gmbh.de - www.ibb-gmbh.de ibb CUTTING TOOLS

Kopfdaten
Prüfer
T. Zikoll

Messergebnisse

| Name | Actual | Nominal | HiTol | LoTol | Status |
|---|---|---|---|---|---|
| L1 | 2.487 mm | 2.500 mm | 0.000 mm | 0.000 mm | |
| L2 | 4.488 mm | 4.500 mm | 0.000 mm | 0.000 mm | |
| L5 | 6.985 mm | 7.000 mm | 0.000 mm | 0.000 mm | |
| L6 | 8.982 mm | 9.000 mm | 0.000 mm | 0.000 mm | |
| L7 | 10.982 mm | 11.000 mm | 0.000 mm | 0.000 mm | |
| L8 | 12.979 mm | 13.000 mm | 0.000 mm | 0.000 mm | |
| L9 | 14.984 mm | 15.000 mm | 0.000 mm | 0.000 mm | |
| L10 | 18.356 mm | 18.500 mm | 0.000 mm | 0.000 mm | |
| D1 | 2.071 mm | 2.000 mm | 0.000 mm | 0.000 mm | |
| D2 | 3.251 mm | 3.200 mm | 0.000 mm | 0.000 mm | |
| D3 | 4.044 mm | 4.000 mm | 0.000 mm | 0.000 mm | |
| Spiralsteigung Ø2 | 23.698 mm | 0.000 mm | 0.000 mm | 0.000 mm | |
| Spiralwinkel Ø2 | 15.172 ° | 0.000 ° | 0.000 ° | 0.000 ° | |
| Spiralsteigung Ø3,2 | 22.434 mm | 0.000 mm | 0.000 mm | 0.000 mm | |
| Spiralwinkel Ø3,2 | 24.324 ° | 0.000 ° | 0.000 ° | 0.000 ° | |
| Spiralsteigung Ø4 | 22.125 mm | 0.000 mm | 0.000 mm | 0.000 mm | |
| Spiralwinkel Ø4 | 29.715 ° | 0.000 ° | 0.000 ° | 0.000 ° | |
| Kerndurchmesser Ø2 | 0.953 mm | 0.000 mm | 0.000 mm | 0.000 mm | |
| Spanraumtiefe Ø2 | 0.554 mm | 0.000 mm | 0.000 mm | 0.000 mm | |
| Spanwinkel (0.100 mm) Ø2 | -6.675 ° | 0.000 ° | 0.000 ° | 0.000 ° | |
| Kerndurchmesser Ø3,2 | 0.875 mm | 0.000 mm | 0.000 mm | 0.000 mm | |
| Spanraumtiefe Ø3,2 | 1.186 mm | 0.000 mm | 0.000 mm | 0.000 mm | |
| Spanwinkel (0.200 mm) Ø3,2 | -0.517 ° | 0.000 ° | 0.000 ° | 0.000 ° | |
| Kerndurchmesser Ø4 | 1.008 mm | 0.000 mm | 0.000 mm | 0.000 mm | |
| Spanraumtiefe Ø4 | 1.514 mm | 0.000 mm | 0.000 mm | 0.000 mm | |
| Spanwinkel (0.200 mm) | 29.635 ° | 0.000 ° | 0.000 ° | 0.000 ° | |
| A1 | 118.927 ° | 60.000 ° | 0.000 ° | 0.000 ° | |
| A2 | 60.916 ° | 0.000 ° | 0.000 ° | 0.000 ° | |
| A3 | 58.902 ° | 0.000 ° | 0.000 ° | 0.000 ° | |
| Spitzenwinkel | 118.154 ° | 0.000 ° | 0.000 ° | 0.000 ° | |
| Spitzenwinkel Proj. (Kontollmessung) | 117.634 ° | 0.000 ° | 0.000 ° | 0.000 ° | |
| Spanwinkel, Stirn | -0.330 ° | 0.000 ° | 0.000 ° | 0.000 ° | |
| 1. Freiwinkel, Stirn | 28.654 ° | 0.000 ° | 0.000 ° | 0.000 ° | |
| 1.Freiwinkel, Stirn (Kontrollmessung) | 32.584 ° | 0.000 ° | 0.000 ° | 0.000 ° | |
| Schneide vor Mitte | 0.013 mm | 0.000 mm | 0.000 mm | 0.000 mm | |

| Messprogramm | | geprüft am | |
|---|---|---|---|
| Bur_Ø4,0_New | | | |
| Kunde | | Programmordner | |
| ... | | Auto-Check | |
| Messung Nummer | Seite | Unterschrift | |
| 1 | 1 von 2 | | |

FIG. 13

MULTI-DIAMETER DRILL BIT

CROSS-REFERENCE TO RELATED APPLICATIONS

This application claims the benefit of U.S. Provisional Application No. 62/183,448 filed on Jun. 23, 2015, the entire contents of which are incorporated herein by reference.

BACKGROUND

The present disclosure relates to universal drills that can be applied to implant surgery, bone drilling or metal drilling. More particularly, the present disclosure relates to drill bits, which are capable of decreasing friction for safer and more predictable results.

The insertion of dental implants commonly involves previous drilling and tapping procedures using multiple surgical implant drill bits of varying diameters for the conformation of an implant bed. The main purposes of the drilling, among others, are the fixation of the implant at the apical portion and/or at the lateral walls of the surrounding bone and the establishment of primary stability. Multiple surgical implant drill bits are used with the intention of avoiding excessive temperatures in the bone tissue that is being prepared for receiving a dental implant. However, regardless of the drilling technique, drilling materials, drill geometry or bone characteristics, some degree of thermal and mechanical injuries can occur.

During the drilling procedures, some temperature rises are due to friction of the drill in contact with surrounding bone tissue, such as bone walls or bone fragments. If the bone temperature is higher than 47° C. for 1 minute, human bone cells will show damage, necroses, apoptoses and be replaced by connective tissue. This will not result in the necessary biologic stability for long term implant success. A certain amount of mechanical or primary stability is needed instantaneously after surgery. This primary stability depends on the bone quality and quantity, the implant threads and implant body design and the implant bed preparation procedure. Therefore, the implant bed preparation executed with the specific implant drill bits needs to be as minimally invasive, accurate and precise as possible.

The thermal and mechanical damage which is produced by the drilling procedure has been associated with a combination of different variables including drill speed, feed rate, drill diameter, drill geometry, drill design, irrigation, drilling depth and drilling pressure.

Over seventy percent of all energy that is delivered by a drill, its surface and down hole equipment to drill an implant bed is lost through friction. Friction reducers, or as commonly referred to in the drilling industry, lubricants, can help to alleviate friction. The three problems that are common with the use of standard lubricants are compatibility, efficacy and biologic compliance. Although the simplest lubricant (sterile saline solution) is commonly used in implant surgery, its effect is limited due to the in-vivo environment and constraints that go hand-in-hand with working on the human body. Because lubricant is not fully successful in solving the issue due to its inherent limitations, the drill design should be altered to reduce the friction.

Every implant drill loses power through friction. This friction results from the operating surface of standard mechanical drill bits being in close contact to surrounding hard tissue. Operational efficiencies are tremendously hindered by only delivering a fraction of the energy that is placed into the well to drill, trip and complete. Friction is the function of the reactive forces that are a result of two bodies rubbing against each other. This is the rubbing of wear components at the surface of the rig, the sliding and rotation of drill string components and casing against bone formation. Down hole friction is polynomial where there are several drilling functions that can contribute to the increase in friction. The three main contributors (responsible for at least 95% of friction below the rotary table) are drilling torque, drilling drag and flowing pressure losses.

The two most important items for an implant drill bit are drilling torque and drilling drag. Drilling torque (angular friction) is generated when the drill bit is rotated while conducting drilling operations such as drilling ahead or back reaming During rotational drilling, drilling torque accounts for a majority of the energy lost through friction. If left unmitigated, drilling torque can bring the drilling process to a halt. When drilling torque approaches or exceeds the rig's rotary (top drive or rotary table) capability, the drilling process becomes very limited or even ceases if left unmitigated. The ability to rotate is necessary to break the static friction that exists between the drill bit-to-casing (Guided Surgery) or drill bit-to-bone. The inability to rotate effectively manifests at slower drilling rates and poor hole cleaning, which can lead to even higher friction, lost circulation and stuck drills. Also rotating the drill bit continuously at higher torque can lead to more frequent surface equipment failures, down hole equipment failures, casing wear and drill bit failures. Drilling drag (axial friction) is generated as the drill bit slides against the surrounding material formation or casing.

Therefore, there is a need for improved implant drill bits to achieve decreased friction for safer and more predictable and precise implant bed preparations in patients' bones, while also decreasing the time required to complete the preparation by decreasing the number of surgical drill bits needed.

SUMMARY

According to an exemplary aspect of the present disclosure, a multi-diameter drill bit for implant bed preparation is provided. The multi-diameter drill bit extends longitudinally along an axis. The multi-diameter drill bit includes a drill shank configured to be coupled with a driving tool used by an operator. The drill shank is proximal to an operating hand of the operator. The multi-diameter drill bit also includes a drill body distal to the drill shank, which includes at least a first cylindrical portion and a second cylindrical portion. The first cylindrical portion has a first diameter and the second cylindrical portion has a second diameter. The first cylindrical portion is distal to the second cylindrical portion. The multi-diameter drill bit further includes a drill tip distal to the first cylindrical portion of the drill body. The drill tip defines a plurality of first land areas and a plurality of cutting lips at least partially bordering the plurality of first land areas, respectively. The drill shank is configured to transfer drilling torques and forces generated by the driving tool to the drill body and the drill tip. The second diameter of the second cylindrical portion is greater than the first diameter of the first cylindrical portion to define a plurality of faces of second lands at the interface between the first cylindrical portion and the second cylindrical portion. The faces of second lands are configured to reduce friction between the drill bit and surrounding bone tissue. Each of the plurality of faces of second lands includes a curved margin.

BRIEF DESCRIPTION OF THE DRAWINGS

FIG. 13 is a table showing actual dimensions of a multi-diameter (4.0 mm) drill bit according to an exemplary embodiment of the disclosure.

DETAILED DESCRIPTION OF EXEMPLARY EMBODIMENTS

Figure 1:
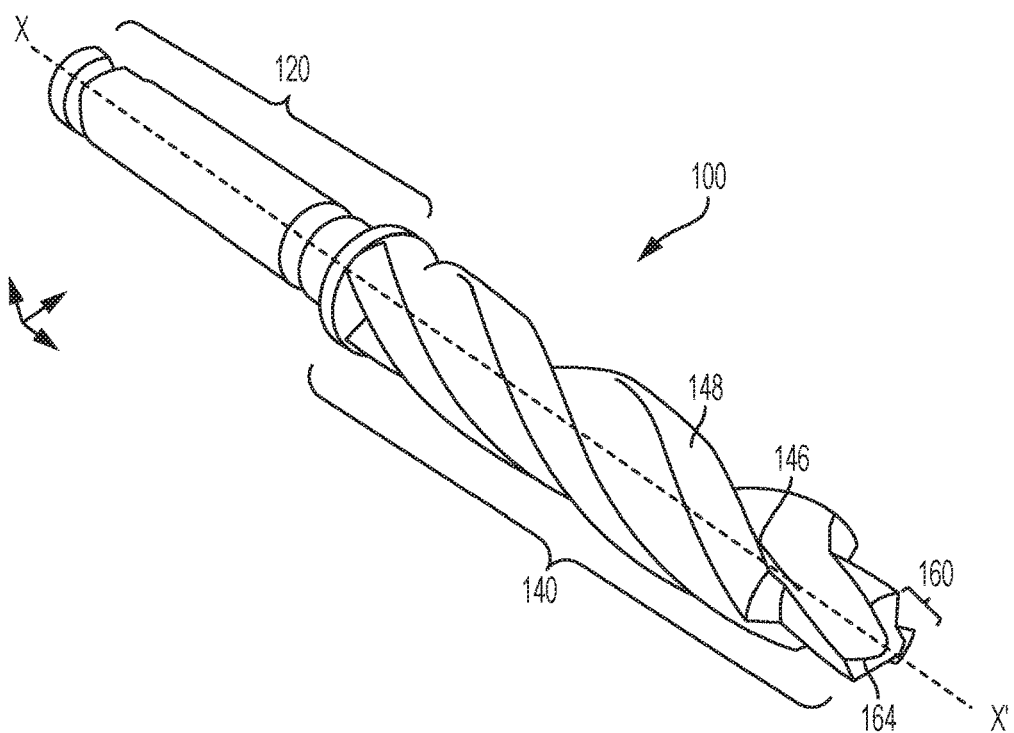
FIG. 1 is a perspective view showing a multi-diameter drill bit according to an exemplary embodiment of the disclosure.

Detailed embodiments of the present disclosure are described herein; however, it is to be understood that the disclosed embodiments are merely illustrative of the compositions, structures and methods of the disclosure that may be embodied in various forms. In addition, each of the examples given in connection with the various embodiments is intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the compositions, structures and methods disclosed herein. References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment.

FIGS. 1-4 depict a multi-diameter drill bit 100 according to an embodiment of the disclosure. The multi-diameter drill bit 100 is substantially elongated and extends longitudinally along an axis X-X'. Along the extension of the axis X-X', the multi-diameter drill bit 100 is substantially divided into three functional parts, i.e., a drill shank 120 that is approximate to an operating hand of an operator, a drill body 140 distally connected to the drill shank 120, and a drill tip 160 distally connected to the drill body 140.

The drill shank 120 is typically cylindrical and can be operatively coupled to a surgical driving tool to allow drilling torques and forces to be applied to the shank 120 and subsequently, transferred to the drill body 140 and the drill tip 160. For example, the cylindrical drill shank 120 can have a length of 14 mm and a diameter of 2.35 mm The drill body 140 includes a first cylindrical portion 142 and a second cylindrical portion 144 integrally formed with each other. The first cylindrical portion 142 and the second cylindrical portion 144 are configured in a cylindrical shape. However, in an embodiment of the disclosure, the first cylindrical portion 142 and the second cylindrical portion 144 may be configured in a conical shape or other suitable shape. The first cylindrical portion 142 has a first length L1 and a first diameter RE The second cylindrical portion 144 has a second length L2 and a second diameter R2. In the shown embodiment, the first length L1 is smaller than the second length L2; the first diameter R1 is smaller than the second diameter R2. For example, the first length L1 can be 2.5 mm and the second length can be 16 mm The first diameter R1 can be 2 mm and the second diameter R2 can be 3.2 mm; alternatively, the first diameter R1 can be 2.3 mm and the second diameter R2 can be 3.3 mm; alternatively, the first diameter R1 can be 2.5 mm and the second diameter R2 can be 4.1 mm A plurality of helical flutes 146 and a plurality of helical lands 148, which are provided circumferentially alternatively with respect to each other, extending from the drill tip 160 to the drill shank 120. The plurality of helical flutes 146 maintain their shape and geometry from the drill tip 160 to the drill shank 120. That is, while the first diameter R1 is different from the second diameter R2 from the drill tip 160 to the drill shank 120, the plurality of helical flutes 146 have a uniform shape and geometry from the drill tip 160 to the drill shank 120. During a drilling operation, the plurality of helical flutes 146 functions to channel out swarf and/or bone debris, which are produced from a machining surface and/or cutting edges of the multi-diameter drill bit 100 when the drilling torque and force are applied to the drill shank 120. In the shown embodiment, three helical flutes and three helical lands are alternatively disposed with respect to each other. Depending on the circumstances of using the drill bit, the multi-diameter drill bit 100 may be configured to provide different numbers of alternative helical flutes and lands. For example, the number of the flutes and lands can be in a range from 2 to 6.

Figure 2:
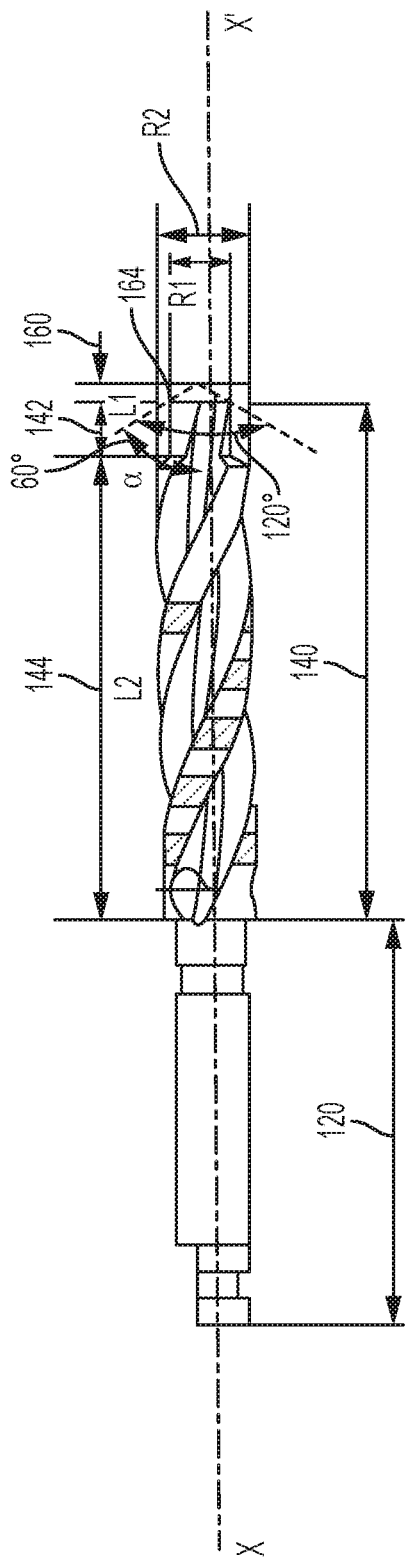
FIG. 2 is a front elevation view of the multi-diameter drill bit of FIG. 1.
Figure 4:
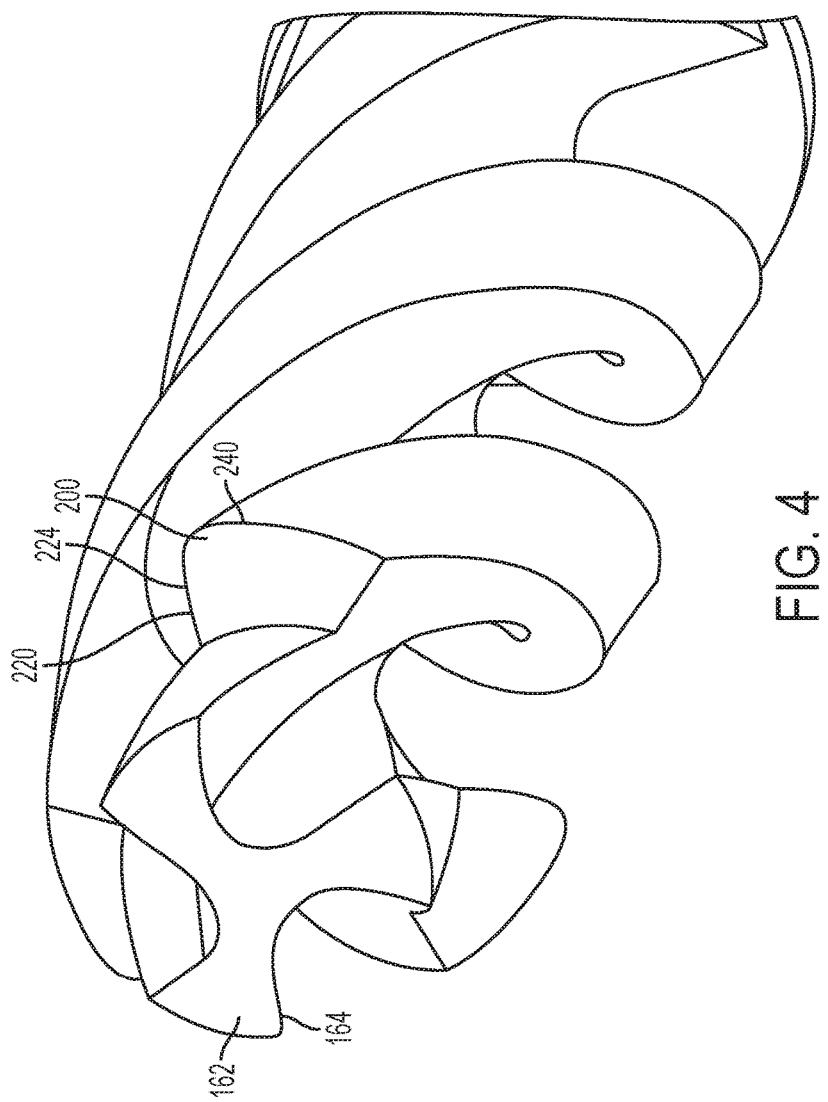
FIG. 4 is an enlarged perspective view showing the distal end of the multi-diameter drill bit of FIG. 1.

As best shown in FIG. 4, the drill tip 160 defines a plurality of first land areas 162 and a plurality of first cutting lips 164 at least partially bordering the plurality of first land areas 162, respectively. The first land areas 162 and the first cutting lips 164 together form a machining mechanism of the drill bit 100 during a drilling operation. As shown in FIG. 2, each of the first cutting lips 164 forms an angle $\alpha$ with respect to the axis X-X', which angle is in a range of 45° to 75°. In the shown embodiment, the angle $\alpha$ is 60°. In the shown embodiment depicted in FIG. 2, the point angle is 120°. In further embodiments, the point angle is about 115° to about 125°. Thus, the point angle may be about 115°, 116°, 117°, 118°, 119°, 120°, 121°, 122°, 123°, 124° or about 125°.

The second cylindrical portion 144 of the drill body 140 includes a plurality of faces of second lands 200 defined at the interface between the first cylindrical portion 142 and the second cylindrical portion 144. Each of the faces of second lands 200 extends radially and circumferentially. Each face of second lands 200 has a respective second cutting lip 220.

Figure 3:
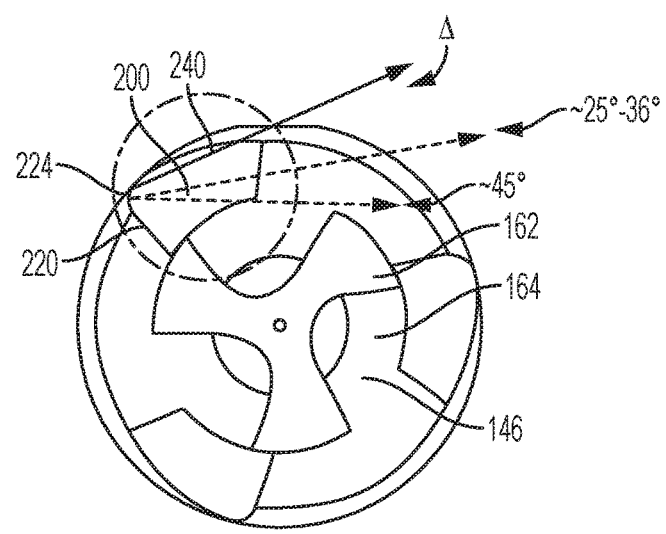
FIG. 3 is an end view showing a distal end of the multi-diameter drill bit of FIG. 1, which end is distanced from a operating hand of an operator during a drilling operation.

The faces of second lands 200 are shaped and dimensioned to reduce the overall friction between the multi-diameter drill bit 100 and surrounding bone. For example, the faces of second lands 200 can be rounded axially with respect to the axis X-X'. Alternatively, the faces of second lands 200 can be sloped proximally from the first cylindrical portion 142 of the drill body 140. By having the rounded or sloped configuration of the faces of second lands, the multi-diameter drill bit 100 is capable of significantly reducing or even minimizing surface contact between the faces of second lands and/or land areas of the drill bit 100 and the surrounding bone, compared to a known drill bit, which has a constant radius and the land areas of which are maintained in close contact with the surrounding bone at all time during a drilling operation. As shown in FIG. 3, the second cutting lip 220 has a curved margin 224 that is at the radial terminal end of the second cutting lip 220. Compared with conventional design of drill bit margins that are straight and prominent portions of the second lands, the curved margin 244 is rounded off. As known in the industry, a margin of a drill bit refers to a narrow portion of a land of the drill bit, which narrow portion is maintained to provide clearance. Provision of the margins serves to stabilize the drill bit in a hole. In addition, each face of second lands 200 also has a radially inwardly curved circumferential edge 240, which is continuous to the curved margin 224. The curved margin 224 and the inwardly curved circumferential edge 240 are formed by properly processing the helical flutes 146 and helical lands 148. In the shown embodiment in FIG. 3, the angle Δ between the curved margin 224 and the inwardly curved circumferential edge 240 is about 28°. In further embodiments, the angle Δ can be about 25° to about 36°. Thus, angle Δ can be about 25°, 26°, 27°, 28°, 29°, 30°, 31°, 32°, 33°, 34°, 35° or 36°. In further embodiments, the angle Δ can be about 1° to about 45°. When the angle Δ is about 1°, the curved margin 224 is slightly curved. When the angle Δ is about 45°, the curved margin 224 recedes to approximately the diameter of the outermost point of the first cutting lips 164.

In the shown embodiment, the drill body 140 includes two cylindrical portions (i.e., the first portion 142 and the second portion 144) with different diameters to provide a stepped structure of the drill body. However, the multi-diameter drill bit, according to the disclosure, may have multiple same or similar stepped structures. For example, FIG. 5 depicts a multi-diameter drill bit 500 according to another exemplary embodiment of the disclosure.

Figure 5:
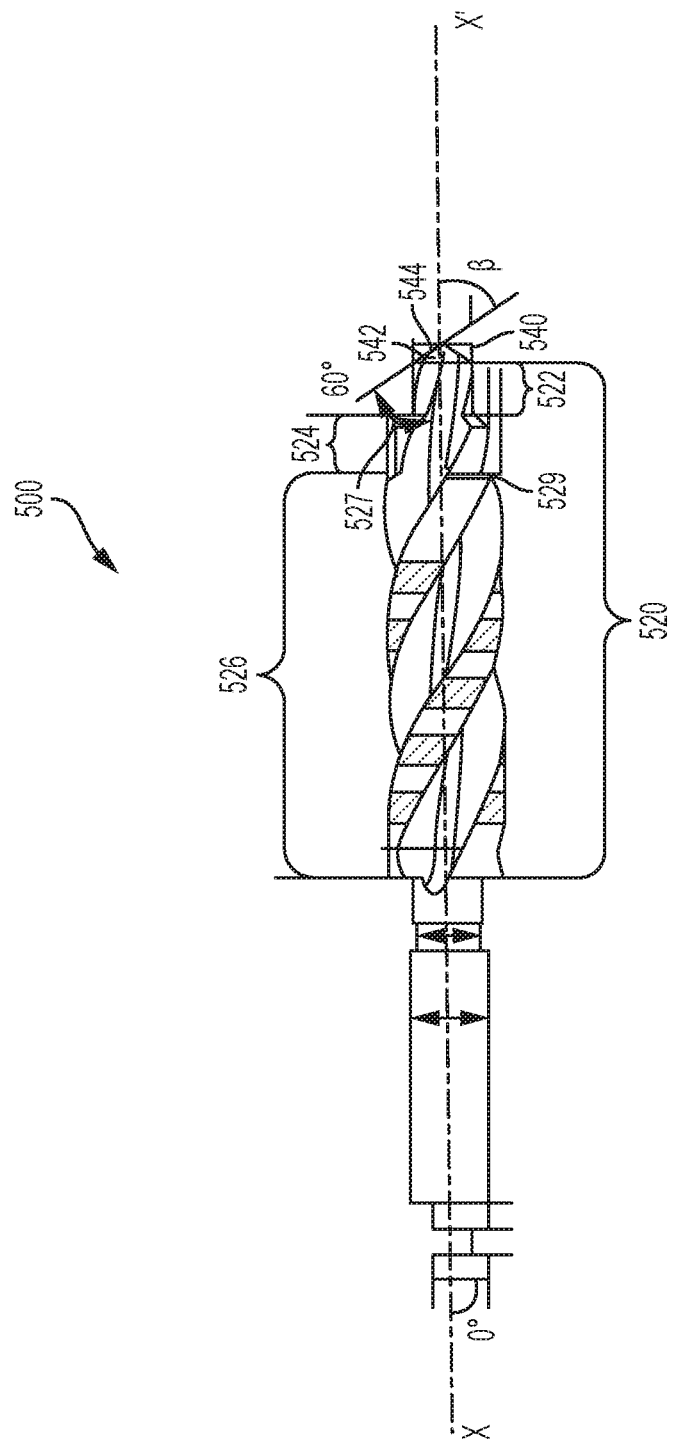
FIG. 5 is a front elevation view showing a multi-diameter drill bit according to another exemplary embodiment of the disclosure.
Figure 6:
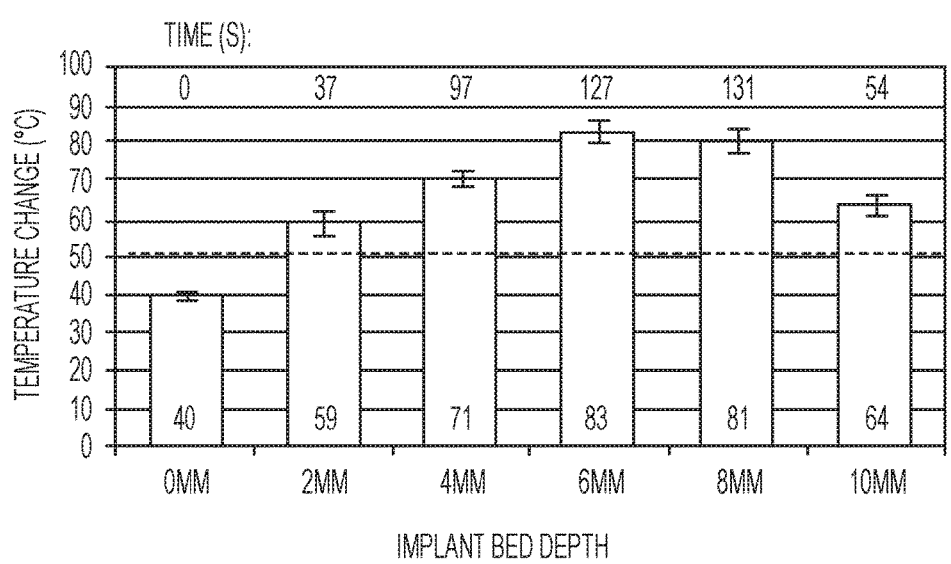
FIGS. 6-8 are graphs showing temperature change for conventional, single step drill bits.
Figure 7:
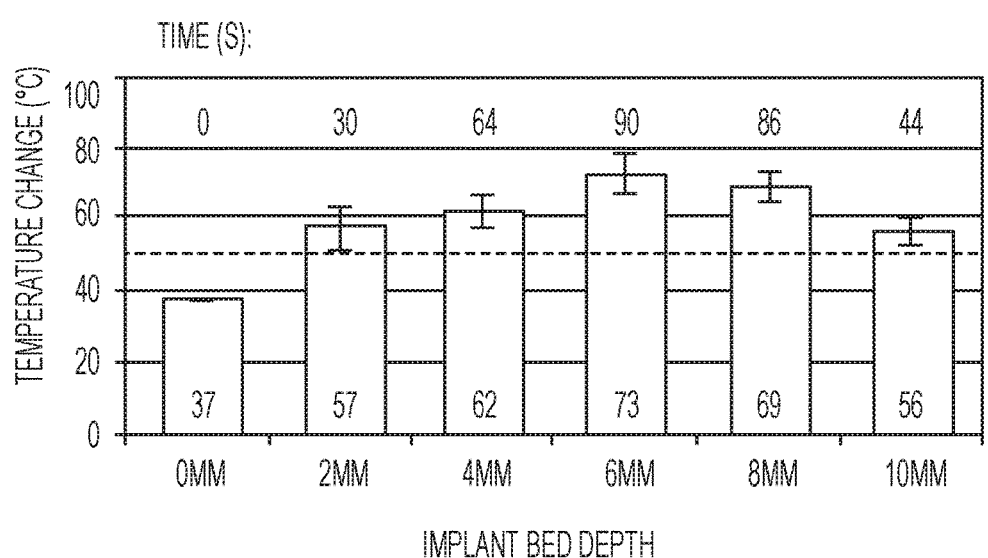
Figure 8:
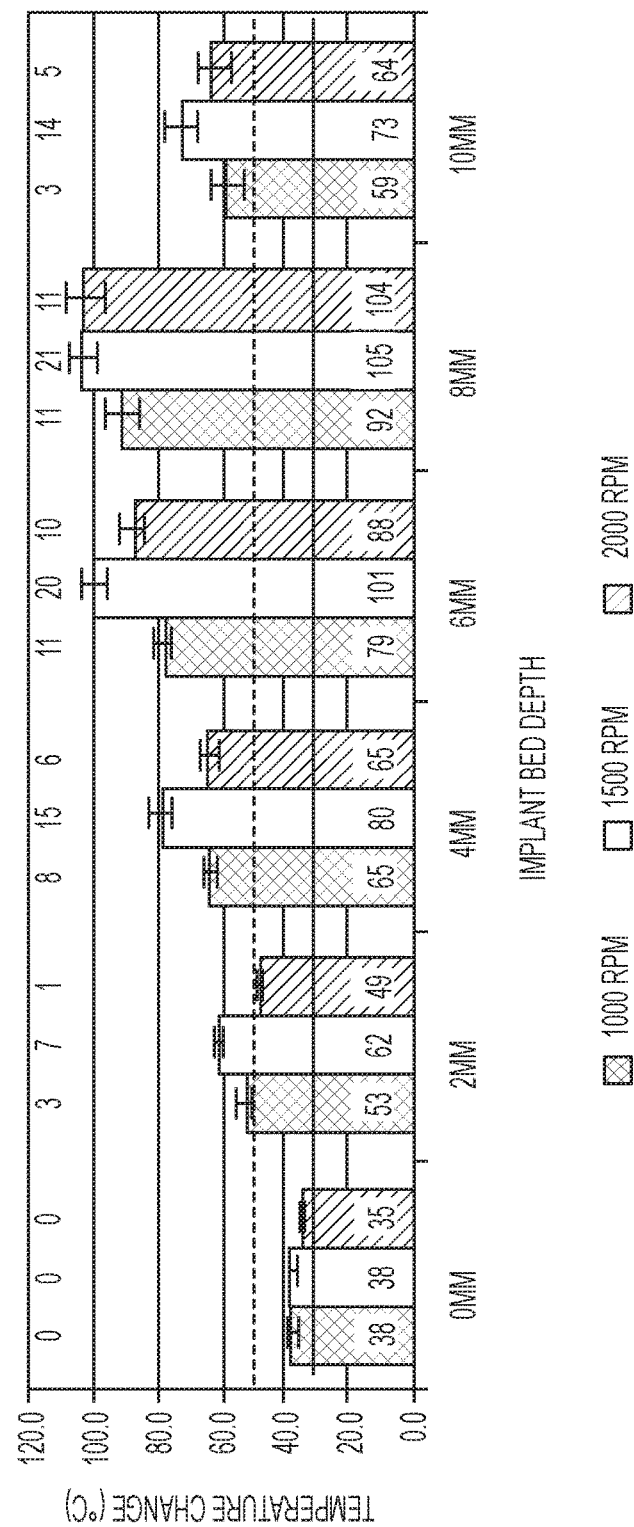

As shown in FIG. 5, the multi-diameter drill bit 500 includes a drill body 520 and a drill tip 540. The drill tip 540 defines a plurality of first land areas 542 and a plurality of first cutting lips 544 at least partially bordering the plurality of first land areas 542, respectively. Each of the first cutting lips 524 forms an angle β with respect to the axis X-X', which angle is in a range of 45° to 75 °. In the shown embodiment, the angle is 60°.

The drill body 520 is divided along the longitudinal axis of the drill bit into a first portion 522 having a first diameter, a second portion 524 having a second diameter and a third portion 526 having a third diameter. The second diameter is greater than the first diameter, such that a first stepped structure is provided at the interface between the first portion 522 and the second portion 524. The third diameter is greater than the second diameter, such that a second stepped structure is provided at the interface between the second portion 524 and the third portion 526.

At the second stepped structure, a plurality of faces of second lands 527 are provided, which faces can be the same or similar to the faces of second lands 200 of the multi-diameter drill bit 100. At the first stepped structure, a plurality of faces of third lands 529 are provided, which faces can be the same or similar to faces of second lands 200 of the multi-diameter drill bit 100. The faces of second lands 527 are distal with respect to the third faces of lands 529. The second and third faces of lands are provided to reduce or minimize surface contact between the land areas of the multi-diameter drill bit 500 and the surrounding bone. As a result, the friction caused by the multi-diameter drill bit 500 can be reduced, which advantageously leads to less heat accumulation and less thermal cell damage to the bone structure (e.g. bone tissue) contacted by the drill bit. For example, the first portion 522 can have a diameter of 2.0 mm; the second portion 524 can have a diameter of 3.2 mm; the third portion 526 can have a diameter of 4.0 mm For example, the first portion 522 can have a length of 2.5 mm; the second portion 524 can have a length of 2 mm; and the third portion 526 can have a length of 14 mm.

According to another embodiment of an aspect of the disclosure, the multi-diameter drill bit can be a subland drill bit, in which two or more drill bits, each having a distinct diameter, are built into a single body. Each component having its respective diameter maintains its own characteristics and geometry. A subland drill bit can be used for drilling two or more holes of distinct diameters in one operation. An independent set of lands is provided extending the entire flute length for each component presented in the drill bit. For example, the subland drill may contain one flute for each component, which extends to the shank. The subland drill bit maintains the individual geometries of each component, and has satisfactory debris (e.g., chips) carrying capability. As a result, a hole having a clean face can be achieved, due to the satisfactory debris evacuation. According to this embodiment, at the interface(s) of the drill bit portions having different diameters, at least one set of faces of lands are provided. These faces of lands are the same or similar to the faces of lands of the multi-diameter drill bit 100 or the multi-diameter drill bit 500. In addition to the typical benefits provided by the subland drill bit, the provision of the faces of lands offers the benefits of reducing friction caused by the drill bit and reducing heat accumulation and thermal cell damage.

According to yet another embodiment of an aspect of the disclosure, a parabolic flute design can be incorporated into the multi-diameter drill bit. In this embodiment, the parabolic flute design provides a more condensed or tighter spiral, resulting in more number of turns based on a predetermined length of the drill bit body (for example, the drill bit body 140 or the drill bit body 520). Thus, the debris removal ability of the multi-diameter drill bit can be further enhanced to allow deeper hole-drilling of the drill bit. The parabolic helix angle of the drill bit can be in a range of 24°-36°. The parabolic flute design allows more grip of the multi-diameter drill bit and avoids the need for pre-drilled holes in a surgical operation. The parabolic flute design can be incorporated into any embodiment of the multi-diameter drill bit of the disclosure, such as a drill bit having a diameter of 4.1 mm According to this embodiment, the faces of lands are similarly provided to the multi-diameter drill bit. Thus, in addition to the typical benefits provided by the parabolic-flute drill bit, the provision of the faces of lands offers the benefits of reducing friction caused by the drill bit and reducing heat accumulation and thermal cell damage.

According to a still further embodiment of an aspect of the disclosure, a multi-diameter drill bit system is provided. The multi-diameter drill bit system includes the multi-diameter drill bit 100, as described in the present disclosure, and a dental implant (not shown). The dental implant is configured to substantially correspond to the shape of the multi-diameter drill bit 100. That is, the dental implant includes multiple stages, e.g., stepped structures. For example, the dental implant includes a first stage, a second stage, and a third stage. The first stage corresponds to the drill tip 160, the second stage corresponds to the first cylindrical portion 142, and the third stage corresponds to the second cylindrical portion 144. In other words, the shape of the first stage is configured such that the first stage fits into the hole created by the drill tip 160. The shape of the second stage substantially corresponds to the length L1 and the first diameter R1 such that the second stage is configured to fit into the hole left by the first cylindrical portion 142. The shape of the third stage substantially corresponds to the length L2 and the second diameter R2 such that the third stage is configured to fit into the hole left by the second cylindrical portion 142.

According to certain embodiments, the multi-diameter drill bit system may include a pilot drill bit. The pilot drill bit includes a drill tip having a diameter equal to or less than the first diameter R1. The pilot drill bit is used to create a pilot hole for subsequent drilling by the multi-diameter drill bit 100. Utilizing the pilot drill bit prior to drilling with the multi-diameter drill bit 100 allows an operator of the multi-diameter drill bit system to drill the pilot hole at the appropriate depth and angle. After using the pilot drill bit, the operator drills a larger hole, corresponding to the implant. The operator therefore has the opportunity to make any necessary corrections to angle and depth of the pilot hole when using the multi-diameter drill bit 100 to drill the larger, subsequent, hole.

According to further embodiments, the multi-diameter drill bit system may include an implant that has less than three stages. Furthermore, the multi-diameter drill bit system may include an implant that has only three stages or consists of three stages.

Within the scope of the disclosure, the multi-diameter drill bits may have any suitable number of steps, e.g., different diameters, depending the circumstances of applying the drill bits. For example, the multi-diameter drill bits may have 2-5 stepped structures.

Figure 9:
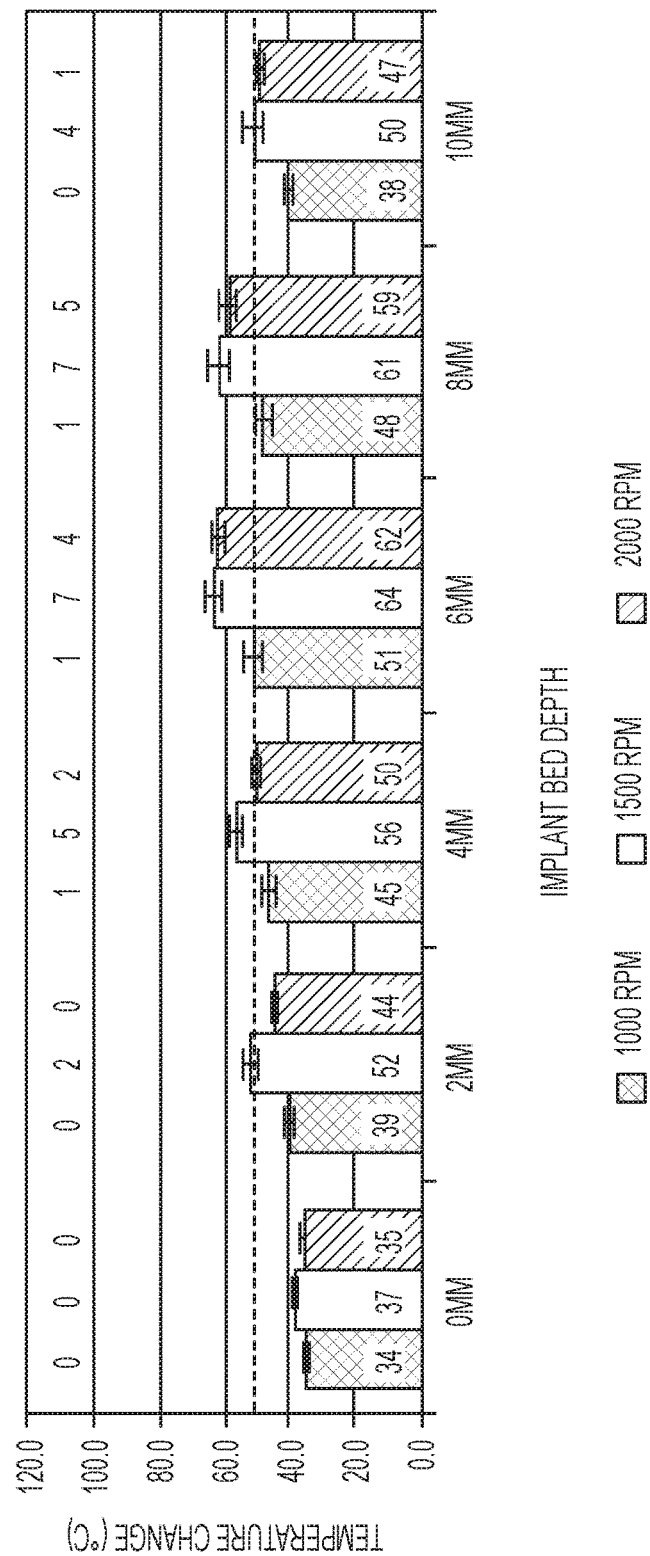
FIGS. 9-12 are graphs illustrating temperature change for use of multi-diameter drill bits having second diameter R2 dimensions of 3.2 mm, 3.3 mm, 4.0 and 4.1 mm, respectively.
Figure 10:
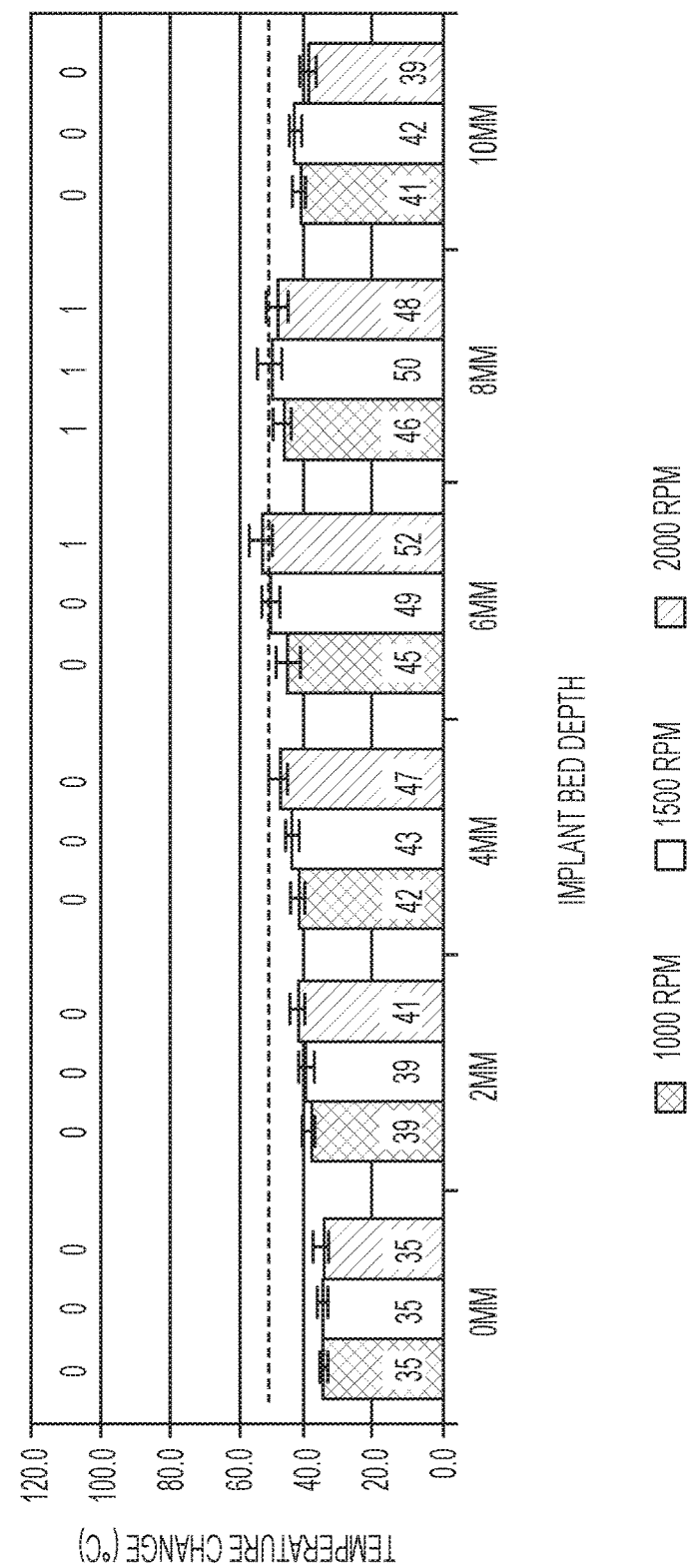
Figure 11:
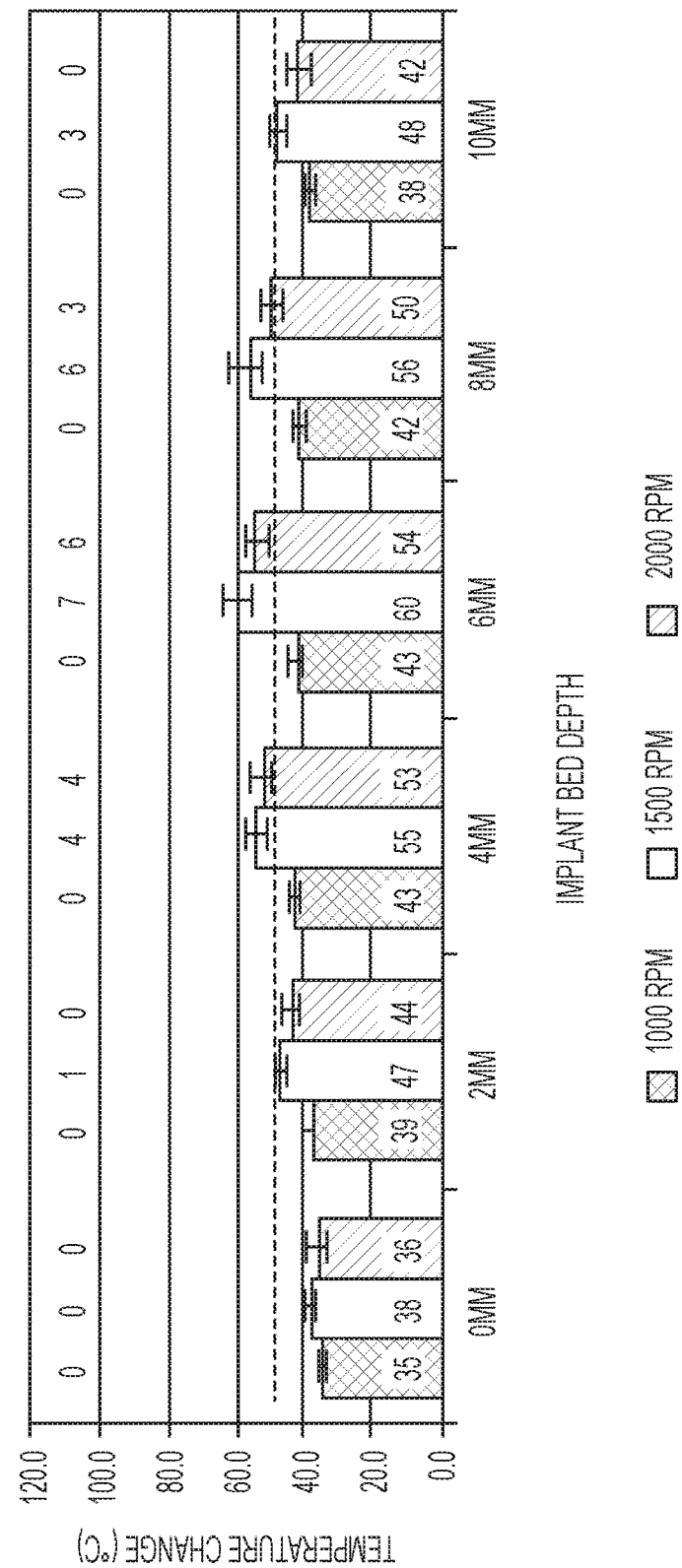
Figure 12:
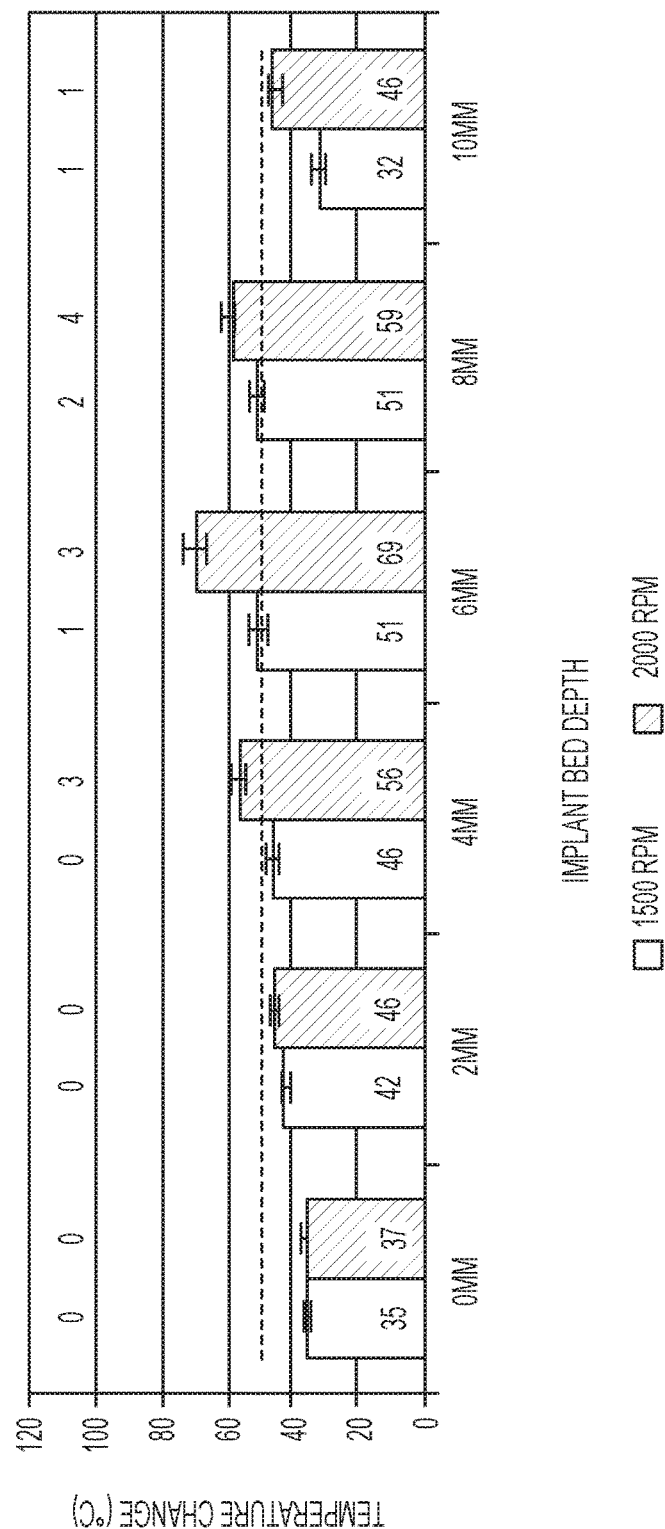
Figure 14:
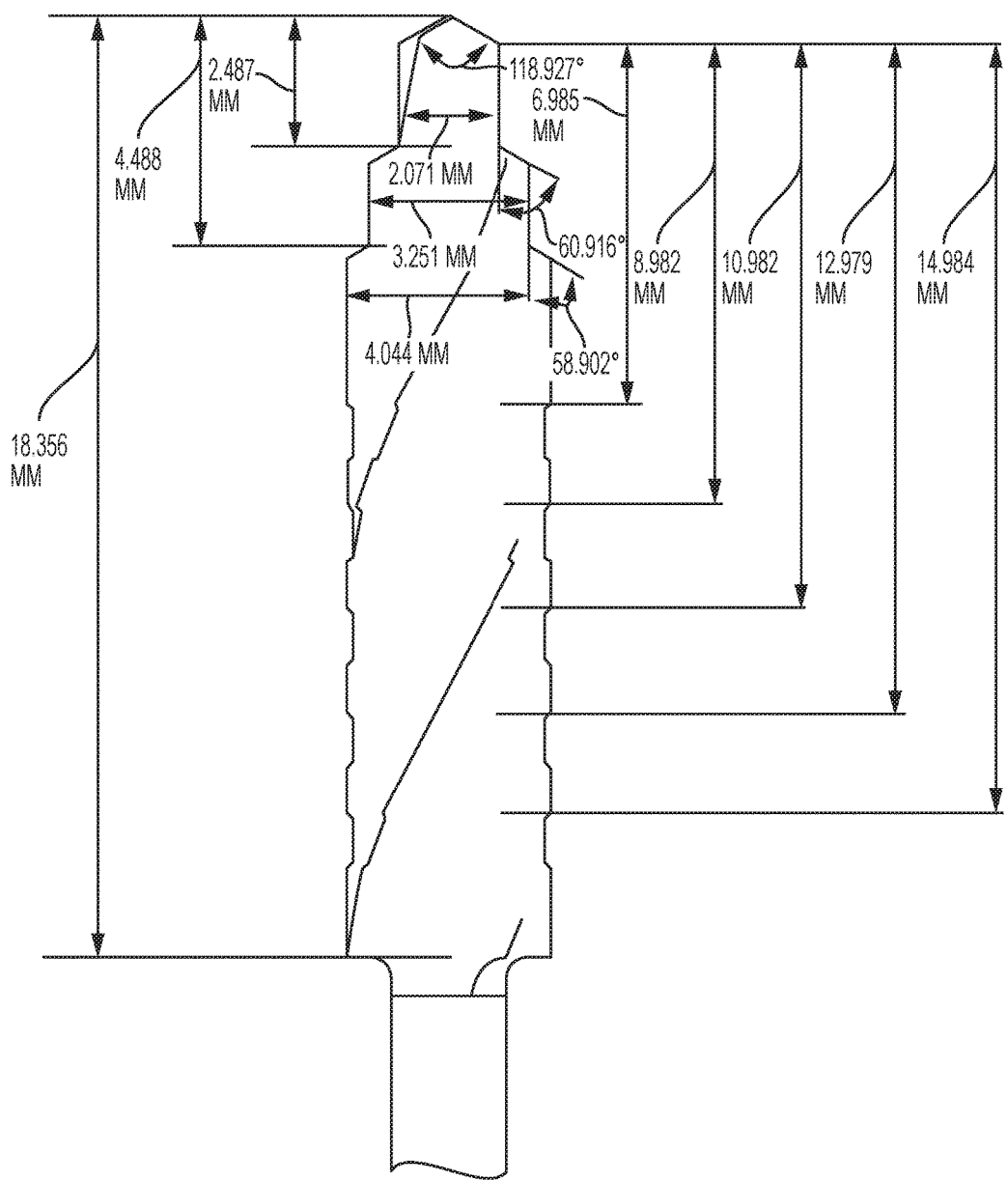
FIG. 14 is a perspective view showing detail of the dimensions of a multi-diameter (4.0 mm) drill bit according to an exemplary embodiment of the disclosure.

Significant advantages can be achieved by the multi-diameter drill bits according to the present disclosure. According to the conventional drilling protocol, a series of 3-5 drill bits each having a constant diameter are typically used chronologically for preparing the implant bed. The multi-diameter drill bit according to the disclosure, such as, the multi-diameter drill bit 100 or the multi-diameter drill bit 500, can be advantageously used in lieu of the conventional sequence of different drill bits, to achieve the same level implant bed preparation. The novel design of the faces of the lands, through the use of a round margin, of the multi-diameter drill bit effectively reduces the contact surface between the drill bit and the surrounding bone tissue and thus, the friction between the drill bit and the surrounding bone tissue, which results in less heat generation and thermal cell damage. As shown in FIGS. 9-11, the multi-diameter drill bit of the present disclosure when employed at spindle speeds of 1000 rpm (2.3 kg load) (FIGS. 9 and 11); and spindle speeds of 1000, 1500 and 2000 (2.3 kg load) (FIG. 10), at all depths observed, did not cause the implant bed to reach the threshold for damage (temperature of 50° C. or more for 30 seconds or longer) 0.5 mm away from the periphery of the drill bit. As shown in FIGS. 9-12, at some depths and spindle speeds, temperatures close to 45° C. are reached (e.g. FIG. 9, 2 mm depth/2000 rpm, 4 mm depth/1000 rpm, 10 mm depth/2000 rpm). Such temperatures have been shown to stimulate bone, allowing for the possibility of enhanced bone apposition, translating into shorter patient healing time. (Dolan et al. J. R Soc. Interface 2012: 9(77): 3504-3513). In contrast, conventional bone level tapered drill bits used at recommended spindle speeds where the 2.2 mm drill bit was used at 800 rpm, the 2.8 mm used at 600 rpm and the 3.5 mm drill bit used at 500 rpm with loads of 1.2 and 2.3 kg produced temperatures that exceeded the threshold of morphological bone damage, i.e. 50° C. or more for 30 seconds or longer. At depths of 4, 6, and 8 mm where temperatures exceeded 60° C., the surrounding bone tissue would be completely damaged.

Furthermore, by using the single multi-diameter drill bit according to the disclosure, treatment time for implant bed preparation can also be reduced significantly. In addition, since there is no requirement for replacing and re-orienting a series of drill bits, the drilling operation implemented by the single multi-diameter drill bit according to the disclosure can be more precise to achieve a clean, round hole. Compared with the conventional drilling protocol, the multi-diameter drill bit according to the disclosure significantly increases implant stability and reduces the possibility for tissue damage in the subject.

The multi-diameter drill bit according to the disclosure is also beneficial for guided surgery, as the drill bit creates less friction and damage to metal sleeves required by the guided surgery. The lands of the multi-diameter drill bit can be coated with a nano-coating, which provides a very smooth surface finish or a higher stability and hardness of the drill bit, particularly when a DLC (diamond like coating) is utilized.

According to the present disclosure, multiple diameter tools are constructed with specific dimensions and geometry that in use perform two or more operations at once. By combining the drill with the tools used for the additional operations, multiple diameter, multi-function tools are created that provide a variety of useful, timesaving benefits. The multi-function tools are capable of improving productivity, saving operational time, increasing accuracy, reducing setup time, minimizing spindle requirements, eliminating tool changes and minimizing part handling. In addition, the multi-diameter drill bit can be used with different dental implants.

According to the present disclosure the multi-diameter drill bit can be can be formed from any bio-compatible or corrosion-resistant substance or composite including, but not limited to: plastic, zirconium, ceramic, polycrystalline diamond, tungsten carbide, titanium, stainless steel or surgical steel. The multi-diameter drill bit of the present disclosure can be reusable or fabricated for a one-time usage.

While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. It is the intention, therefore, to be limited only as indicated by the scope of the claims appended hereto.

What is claimed is:

1. A multi-diameter drill bit for implant bed preparation, the multi-diameter drill bit extending longitudinally along an axis, the multi-diameter drill bit comprising:
   a drill shank configured to be coupled with a driving tool used by an operator, the drill shank being proximal to an operating hand of the operator;
   a drill body distal to the drill shank, the drill body comprising at least a first cylindrical portion and a second cylindrical portion, the first cylindrical portion having a first diameter, the second cylindrical portion having a second diameter, the first cylindrical portion being distal to the second cylindrical portion; and
   a drill tip distal to the first cylindrical portion of the drill body, the drill tip defining a plurality of first land areas and a plurality of first cutting lips at least partially bordering the plurality of first land areas, respectively;
   wherein the drill shank is configured to transfer drilling torques and forces generated by the driving tool to the drill body and the drill tip;
   wherein the second diameter of the second cylindrical portion is greater than the first diameter of the first cylindrical portion to define a plurality of faces of second lands at the interface between the first cylindrical portion and the second cylindrical portion, wherein each of the plurality of faces of second lands is rounded in the direction of the longitudinal axis; and
   wherein each of the plurality of faces of second lands comprises:
   a second cutting lip,
   a curved margin provided at the radial terminal end of the second cutting lip, and
   a circumferential edge, wherein the circumferential edge is curved radially inwardly and continuous to the curved margin.

2. The multi-diameter drill bit according to claim 1, wherein the drill body further comprises a third cylindrical portion proximal to the second cylindrical portion, the third cylindrical portion having a third diameter; and
   wherein the third diameter is greater than the second diameter of the second cylindrical portion to define a plurality of faces of third lands at the interface between the second cylindrical portion and the third cylindrical portion, wherein each of the plurality of faces of third lands comprises a second curved margin.

3. The multi-diameter drill bit according to claim 2, wherein each of the plurality of faces of third lands extends radially and circumferentially with respect to the axis.

4. The multi-diameter drill bit according to claim 2, wherein each of the plurality of faces of third lands comprises a third cutting lip, wherein the second curved margin is provided at the radial terminal end of the third cutting lip.

5. The multi-diameter drill bit according to claim 2, wherein each of the plurality of faces of third lands is rounded axially with respect to the longitudinal axis.

6. The multi-diameter drill bit according to claim 2, wherein each of the plurality of faces of third lands comprises a second circumferential edge, wherein the second circumferential edge is curved radially inwardly and continuous to the second curved margin.

7. The multi-diameter drill bit according to claim 1, further comprising:
   a plurality of helical flutes starting from the drill tip and ending at the drill shank; and
   a plurality of helical lands provided alternatively with respect to the plurality of flutes.

8. The multi-diameter drill bit according to claim 1, wherein each of the plurality of faces of second lands extends radially and circumferentially with respect to the axis.

9. The multi-diameter drill bit according to claim 1, wherein each of the plurality of the first cutting lips forms an angle with respect to the longitudinal axis of the stepped drill bit, the angle being in a range of 45° to 75°.

10. The multi-diameter drill bit according to claim 9, wherein the angle formed by each first cutting lip and the longitudinal axis is 60°.

11. The multi-diameter drill bit according to claim 1, wherein an angle formed between said circumferential edge and said curved margin is about 28°.

12. The multi-diameter drill bit according to claim 1, wherein an angle formed between said circumferential edge and said curved margin is about 1° to about 45°.

13. The multi-diameter drill bit according to claim 1, wherein the plurality of helical flutes comprise a uniform geometry from the drill tip to the drill shank.

* * * * *